United States Patent
Sartor

(10) Patent No.: US 10,713,796 B2
(45) Date of Patent: *Jul. 14, 2020

(54) LOCATING TUMORS USING STRUCTURED LIGHT SCANNING

(71) Applicant: Covidien LP, Mansfield, MA (US)

(72) Inventor: Joe D. Sartor, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/731,226

(22) Filed: Dec. 31, 2019

(65) Prior Publication Data
US 2020/0134832 A1     Apr. 30, 2020

Related U.S. Application Data

(63) Continuation of application No. 15/900,882, filed on Feb. 21, 2018, now Pat. No. 10,521,916.

(51) Int. Cl.
*G06T 7/13* (2017.01)
*A61B 90/98* (2016.01)
(Continued)

(52) U.S. Cl.
CPC .............. *G06T 7/13* (2017.01); *A61B 8/4254* (2013.01); *A61B 34/20* (2016.02); *A61B 90/37* (2016.02); *A61B 90/98* (2016.02); *G06T 7/521* (2017.01); *G06T 7/70* (2017.01); *A61B 2034/107* (2016.02); *A61B 2034/2055* (2016.02); *A61B 2034/2057* (2016.02); *A61B 2034/2065* (2016.02); *A61B 2034/2072* (2016.02); *A61B 2090/373* (2016.02); *A61B 2090/378* (2016.02); *A61B 2090/397* (2016.02); *G06T 2207/10048* (2013.01); *G06T 2207/10132* (2013.01); *G06T 2207/30096* (2013.01); *G06T 2207/30204* (2013.01)

(58) Field of Classification Search
USPC ......................................................... 382/128
See application file for complete search history.

(56) References Cited

U.S. PATENT DOCUMENTS 8,452,375 B2 *   5/2013   Krag ...................... A61B 34/20
                                                              128/899
9,259,290 B2 *   2/2016   Jenkins .................. A61B 5/418
(Continued)

*Primary Examiner* — Ishrat I Sherali

(57) ABSTRACT

Provided in accordance with the present disclosure are systems for identifying a position of target tissue relative to surgical tools using a structured light detector. An exemplary system includes antennas configured to interact with a marker placed proximate target tissue inside a patient's body, a structured light pattern source, a structured light detector, a display device, and a computing device configured to receive data from the antennas indicating interacting with the marker, determine a distance between the antennas and the marker, cause the structured light pattern source to project and detect a pattern onto the antennas. The instructions may further cause the computing device to determine, a pose of the antennas, determine, based on the determined distance between the antennas and the marker, and the determined pose of the antennas, a position of the marker relative to the antennas, and display the position of the marker relative to the antennas.

20 Claims, 4 Drawing Sheets

(51) Int. Cl.
*A61B 8/00* (2006.01)
*A61B 34/20* (2016.01)
*G06T 7/521* (2017.01)
*A61B 90/00* (2016.01)
*G06T 7/70* (2017.01)
*A61B 34/10* (2016.01)

(56) References Cited

U.S. PATENT DOCUMENTS

| | | | |
|---|---|---|---|
| 9,848,950 B2* | 12/2017 | Hezi-Yamit | A61N 7/02 |
| 9,913,733 B2* | 3/2018 | Piron | A61F 2/46 |
| 10,278,779 B1* | 5/2019 | Rudie | A61B 34/20 |
| 10,383,544 B2* | 8/2019 | Fullerton | A61B 5/4312 |
| 10,521,916 B2* | 12/2019 | Sartor | G06T 7/73 |
| 2007/0265491 A1* | 11/2007 | Krag | A61B 17/32053 |
| | | | 600/37 |
| 2011/0313288 A1* | 12/2011 | Chi Sing | A61B 5/0507 |
| | | | 600/437 |
| 2013/0237811 A1* | 9/2013 | Mihailescu | A61B 8/4444 |
| | | | 600/424 |
| 2016/0302880 A1* | 10/2016 | Uhlemann | G01R 33/285 |
| 2016/0324664 A1* | 11/2016 | Piron | A61F 2/46 |
| 2017/0143429 A1* | 5/2017 | Richmond | A61B 5/064 |
| 2017/0258352 A1* | 9/2017 | Wood | A61B 5/0478 |
| 2017/0265947 A1* | 9/2017 | Dyer | A61B 34/20 |
| 2017/0280970 A1* | 10/2017 | Sartor | A61B 5/1076 |
| 2018/0042681 A1* | 2/2018 | Jagga | A61B 90/361 |
| 2018/0104008 A1* | 4/2018 | Dickhans | A61B 34/20 |
| 2018/0303558 A1* | 10/2018 | Thomas | G06F 3/017 |

\* cited by examiner

LOCATING TUMORS USING STRUCTURED LIGHT SCANNING

CROSS-REFERENCE TO RELATED APPLICATIONS

This application is a continuation of U.S. patent application Ser. No. 15/900,882, filed on Feb. 21, 2018. The entire disclosure of the foregoing application is incorporated by reference herein.

BACKGROUND

The present disclosure relates to locating target tissue, such as tumors, lesions, or other areas of interest inside a patient's body, and more particularly, to systems and methods for using structured light scanning to locate the target tissue and determine a distance between the target tissue and a surgical tool.

DESCRIPTION OF RELATED ART

Accurate diagnosis and treatment of diseases such as cancer relies on accurately locating tumors and/or lesions in a patient's body. Localization of tumors and lesions during surgery is often a limiting factor in many surgical procedures, particularly during breast sparing therapy or surgery. While the tumors and lesions may be visualized using various imaging modalities, such as ultrasound, cone beam computed tomography (CBCT), etc., it is often hard for a surgeon to determine the exact location and boundaries of tumors and lesions relative to tools during a surgical procedure. Thus, in an effort to ensure that all cancerous tissue is removed, surgeons may remove significantly more tissue than is necessary to remove the tumor or lesion because they do not know where the exact boundaries of the tumor or lesion are. As such, improvements are needed to aid surgeons with localizing tumors or lesions during surgical procedures. Disclosed hereinbelow are systems and methods for improved localization of tumors and lesions during surgical procedures.

SUMMARY

Provided in accordance with embodiments of the present disclosure are systems for identifying a position of target tissue relative to surgical tools using a structured light detector. In an aspect of the present disclosure, an exemplary system includes an antenna configured to interact with a marker placed proximate target tissue inside a patient's body, a structured light pattern source, a structured light detector, a display device, and a computing device including a processor and a memory storing instructions which, when executed by the processor, cause the computing device to receive first data from the antenna indicating that the antenna is interacting with the marker at a first location, determine a distance between the antenna and the marker at the first location, cause the structured light pattern source to project a pattern onto the antenna, and cause the structured light detector to detect the pattern projected onto the antenna, and generate second data regarding the pattern projected onto the antenna. The instructions may further cause the computing device to determine, based on the second data, a pose of the antenna at the first location, receive third data from the antenna indicating that the antenna is interacting with the marker at a second location, determine a distance between the antenna and the marker at the second location, cause the structured light pattern source to project a pattern onto the antenna, and cause the structured light detector to detect the pattern projected onto the antenna, and generate fourth data regarding the pattern projected onto the antenna. The instructions may further cause the computing device to determine, based on the fourth data, a pose of the antenna at the second location, determine, based on the determined distance between the antenna and the marker at the first location and the second location, and the determined pose of the antenna at the first location and the second location, a position of the marker relative to the antenna, and cause the display device to display the determined position of the marker relative to the antenna.

In another aspect of the present disclosure, the instructions, when executed by the processor, further cause the computing device to receive image data of at least a portion of the patient's body, identify the marker in the image data, identify the target tissue in the image data, determine a position of the target tissue relative to the marker, determine a distance between the antenna and the target tissue, and cause the display device to display the determined distance between the antenna and the target tissue.

In a further aspect of the present disclosure, the distance between the antenna and the target tissue is determined based on the determined position of the target tissue relative to the marker.

In another aspect of the present disclosure, the instructions, when executed by the processor, further cause the computing device to identify an edge of the target tissue in the image data, determine a position of the edge of the target tissue relative to the marker, determine a distance between the antenna and the edge of the target tissue, and cause the display device to display the determined distance between the antenna and the edge of the target tissue.

In a further aspect of the present disclosure, the distance between the antenna and the edge of the target tissue is determined based on the determined position of the edge of the target tissue relative to the marker.

In another aspect of the present disclosure, the system further includes an ultrasound device, the antenna is included in the ultrasound device, and the image data is received from the ultrasound device.

In yet another aspect of the present disclosure, the antenna is a high-gain directional antenna.

In still another aspect of the present disclosure, the antenna is included in a surgical tool.

In yet another aspect of the present disclosure, the antenna is included in an ultrasound device.

In still another aspect of the present disclosure, the marker is a radio frequency identification (RFID) device.

In yet another aspect of the present disclosure, the antenna is a first antenna and a second antenna, and the computing device receives the first data from the first antenna and receives the third data from the second antenna.

In a further aspect of the present disclosure, the first antenna is included in an ultrasound device, and the second antenna is included in a surgical tool.

In another aspect of the present disclosure, determining the pose of the antenna includes determining a position and an orientation of the antenna relative to the structured light detector based on the pattern projected onto the antenna.

In a further aspect of the present disclosure, determining a position and an orientation of the antenna relative to the structured light detector includes determining a distortion of at least a portion of the pattern projected onto the antenna.

In another aspect of the present disclosure, the first and third data include a signal strength metric, and the distance between the antenna and the marker at the first and third locations is determined based on the signal strength metric.

In yet another aspect of the present disclosure, the instructions, when executed by the processor, further cause the computing device to determine an orientation of the marker relative to the antenna based on the first data or the third data.

In still another aspect of the present disclosure, the structured light pattern source and the structured light detector are included in a structured light scanning device.

In yet another aspect of the present disclosure, the structured light detector is an infrared imaging device.

In still another aspect of the present disclosure, the structured light detector is a laser.

In a further aspect of the present disclosure, the laser is an LED laser emitting a collimated beam of light.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

The present disclosure generally relates to systems and methods for localization of target tissue, such as tumors, lesions, or other aberrant structures, in a patient's body. More specifically, the disclosure relates to determining a distance between the target tissue and a surgical tool, and providing guidance to aid surgeons in identifying boundaries of target tissue during surgical procedures. A marker may be placed into or proximate the target tissue, for example, during a biopsy procedure using image guidance. An antenna included in a surgical tool or medical imaging device may interact with the marker to determine one or more of a distance between the antenna and the marker, a direction of the marker relative to the antenna, and an orientation of the marker relative to the antenna. A structured light pattern may be projected onto the surgical tool or medical imaging device including the antenna, and the pattern may be detected by a structured light scanner to determine the surgical tool or medical imaging device's pose relative to the structured light scanner. The position of the target tissue relative to the surgical tool or medical imaging device may then be determined based on the distance between the antenna and the marker, and the position of the marker relative to the target tissue.

Figure 1:
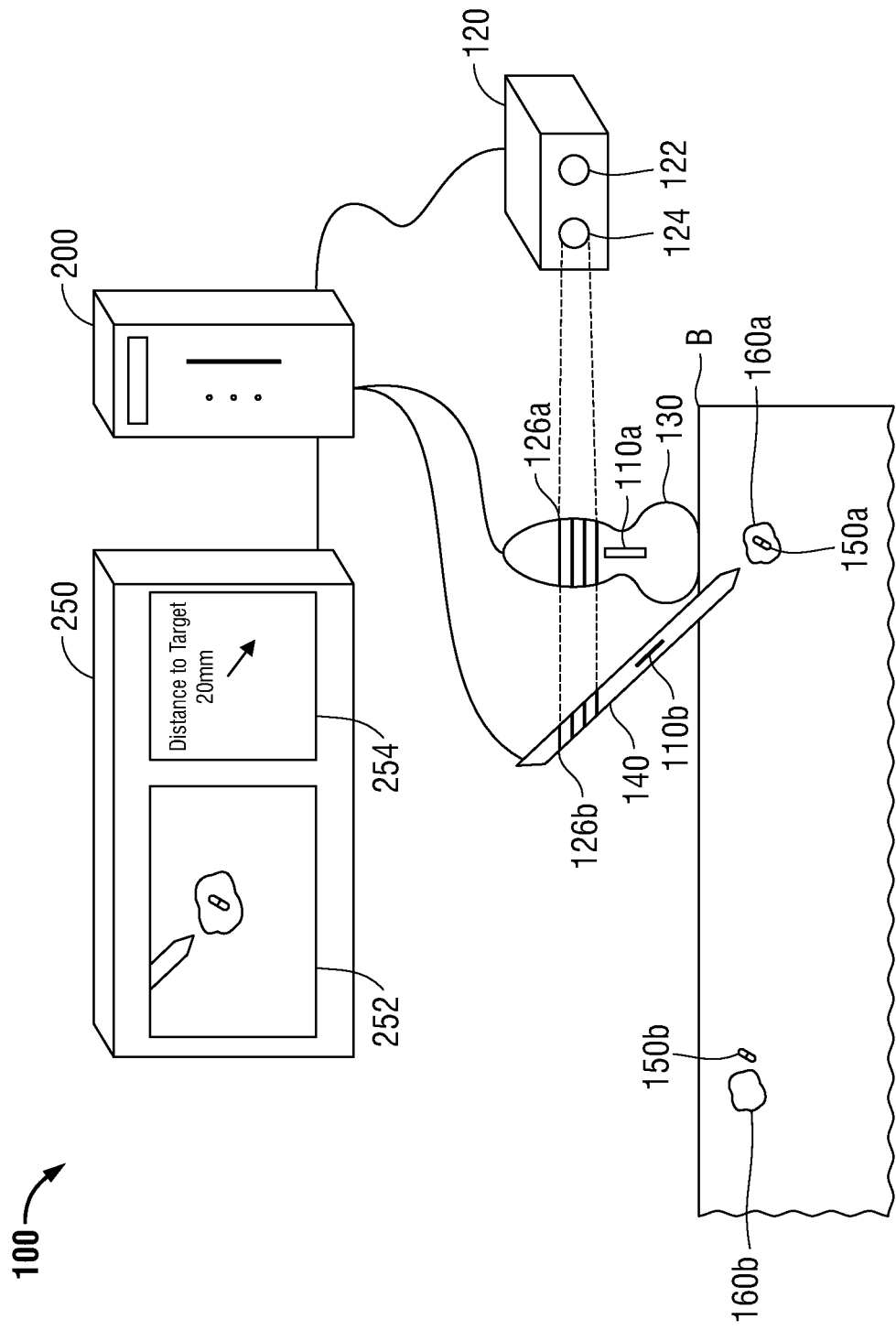
FIG. 1 is a schematic diagram of an exemplary system for locating a target location using structured light scanning, according to an embodiment of the present disclosure.

Turning now to FIG. 1, there is shown an exemplary system 100 usable for localization of target tissue, according to an embodiment of the present disclosure. The system 100 includes at least one antenna 110a, 110b, and a structured light scanning device 120 including a structured light detector 122 and a structured light pattern source 124. The structured light pattern source 124 is configured to project, display, or otherwise emit a pattern 126a, 126b onto objects. The structured light detector 122 is configured to detect the pattern 126a, 126b, and determine a pose of the object relative to the structured light scanning device, as described further below.

In embodiments, the antennas 110a, 110b may be included in, attached to, or otherwise coupled with a medical imaging device, such as an ultrasound probe 130. The antennas 110a, 110b may also be included in, attached to, or otherwise coupled with a surgical tool 140. In other embodiments, the antennas 110a, 110b may be a separate device from the ultrasound probe 130 and the surgical tool 140. In the exemplary embodiment illustrated in FIG. 1, the antenna 110a is included in the ultrasound device 130, and the antenna 110b is included in the surgical tool 140. While the system 100 includes two antennas 110a, 110b, those skilled in the art will appreciate that any number of antennas may be used during a surgical procedure without departing from the scope of the present disclosure. The antennas 110a, 110b may be high gain antennas, directional antennas, and/or any other relevant type of antenna or sensor known to those skilled in the art. Additional examples of sensors include optical near-infrared cameras, magnetometers, radio-frequency time of flight sensors.

As illustrated in FIG. 1, the pattern 126a is projected onto the ultrasound probe 130, and the pattern 126b is projected onto the surgical tool 140. For the purpose of brevity, the patterns 126a, 126b will hereinafter be referred to collectively as "pattern 126." Pattern 126 may be any pattern usable for structured light scanning known to those skilled in the art. In the exemplary embodiment illustrated in FIG. 1, the pattern 126 is a set of parallel lines. As described in further detail below, the pose of the ultrasound probe 130 and/or the surgical tool 140 may be determined based on a width of the lines and the spacing between the lines, as well as distortions in the pattern of the lines as detected by the structured light detector 122.

In the exemplary embodiment illustrated in FIG. 1, the structured light detector 122 and the structured light pattern source 124 are included in a single structured light scanning device 120. In other embodiments, the structured light detector 122 and the structured light pattern source 124 may be separate devices and/or devices placed in different locations about a surgical environment. In further embodiments, multiple structured light detectors 122 and multiple structured light pattern sources 124 may be used. As illustrated in FIG. 1, the structured light detector 122 and/or the structured light pattern source 124 may be positioned such that the pattern 126 may be projected onto to the ultrasound probe 130 and the surgical tool 140. In embodiments, the structured light detector 122 and/or the structured light pattern source may be positioned in any position or orientation about the surgical environment, for example, as part of a lighting structure above the patient and/or in a lateral position relative to the ultrasound probe 130 and the surgical tool 140. The structured light detector 122 and the structured light pattern source 124 may be positioned at an angle from each other. The structured light pattern source 124 may use various lighting techniques to project the pattern 126 onto the ultrasound probe 130 and/or the surgical tool 140. For example, the structured light pattern source may be a Digital Light Processing (DLP) system, a visible light projector, an infrared light projector, and/or a laser such as a light emitting diode (LED) laser. Structured light detector 122 is capable of detecting the pattern 126 by the various lighting techniques used by the structured light pattern source 124.

As will be appreciated by those skilled in the art, the structured light detector 122 may use infrared light to avoid interference from visible light sources. The structured light pattern source 124 may have a known position relative to the structured light detector 122, which permits the calculation of the exact location of the intersection between a light ray emitted by the structured light pattern source 124 and a focus point of the structured light detector 122. The pattern 126 may be detected by the structured light detector 122 as single points, lines, and/or arrays to create topologic maps of surfaces. In embodiments, the structured light pattern source 124 is one or more light emitting diodes (LEDs) or LED infrared lasers that are dispersed into a pattern (line, mesh, or dots), by rotating mirror, beam splitter, or diffraction grating. In one embodiment, the structured light pattern source 124 may be a LED laser configured to emit a collimated beam of light. Use of the structured light detector 122 and the structured light pattern source 124 enables visualization systems to achieve accurate surface maps of the tools used during the surgical procedure and thereby pinpoint their position in space relative to the structured light scanning device 120.

Additionally or alternatively, the structured light pattern source 124 may be a digital light processing (DLP) projection system having a light source, a first lens, one or more mirrors, a DLP chip, and a second lens. In such embodiments, the structured light detector may be a camera spaced apart and angled relative to the second lens of the DLP projection system at known values such that the topography of the surface maps of the tools may be determined using trigonometric functions.

The antennas 110a, 110b are configured to interact with a marker 150a, 150b. The marker 150a, 150b is placed inside a patient's body inside or proximate target tissue 160a, 160b. As shown in FIG. 1, the marker 150a is placed inside the target tissue 160a, and the marker 150b is placed proximate the target tissue 160b. For the purpose of brevity, the markers 150a, 150b is referred to collectively hereinafter as "marker 150." Likewise, the target tissue 160a, 160b is referred to collectively hereinafter as "target tissue 160." The marker 150 may be placed inside or proximate the target tissue 160 using image guidance during a prior surgical procedure and/or during a diagnostic procedure, such as a biopsy. The marker 150 may be a radio frequency identification (RFID) device, a magnetic device, and/or any other marker or fiducial known to those skilled in the art with which the antennas 110a, 110b may interact. The antennas 110a, 110b may determine a distance between the antennas 110a, 110b and the marker 150, such as based on the strength of a signal and/or magnetic force, and/or based on triangulation of the position of the marker 150 relative to the antennas 110a, 110b. For example, in embodiments where the antennas 110a, 110b only provide a signal strength metric, the position of the antennas 110a, 110b determined by the structured light detector 122 enables the computing device 200 to triangulate between a first and at least a second position, and determine the position of the marker 150 relative to the current location of the antennas 110a, 110b based on the signal strength metric. In embodiments where the marker 150 is an RFID device, the marker 150 may provide to the antennas 110a, 110b information stored in the marker 150, such as identification information of the marker 150, e.g. an identification number and/or a date and time when the marker 150 was placed, as well as information relating to the position of the marker 150 relative to the target tissue 160. By providing the identification information, the computing device 200 and/or a clinician using the system 100 may identify a particular marker 150 from among a plurality of markers 150 (e.g. in a situation where multiple lesions are located in close proximity to each other, a particular lesion may be identified based on its associated marker 150). Additionally, in situations involving a large area of target tissue 160, one or more markers 150 may be placed at the boundaries of the target tissue 160 to help identify a particular boundary or limit of the target tissue 160, and the computing device 200 may subsequently identify such boundaries based on the identification information provided by the marker 150.

The system 100 further includes a computing device 200 coupled to or otherwise connected with the structured light scanning device 120, the ultrasound probe 130, the surgical tool 140, and a display device 250. The computing device 200 may be a desktop computer, a laptop computer, a server, and/or any other computing device or multiple computing devices known to those skilled in the art. The display device 250 may be configured to display output generated by the computing device 200, as described further below.

Figure 2:
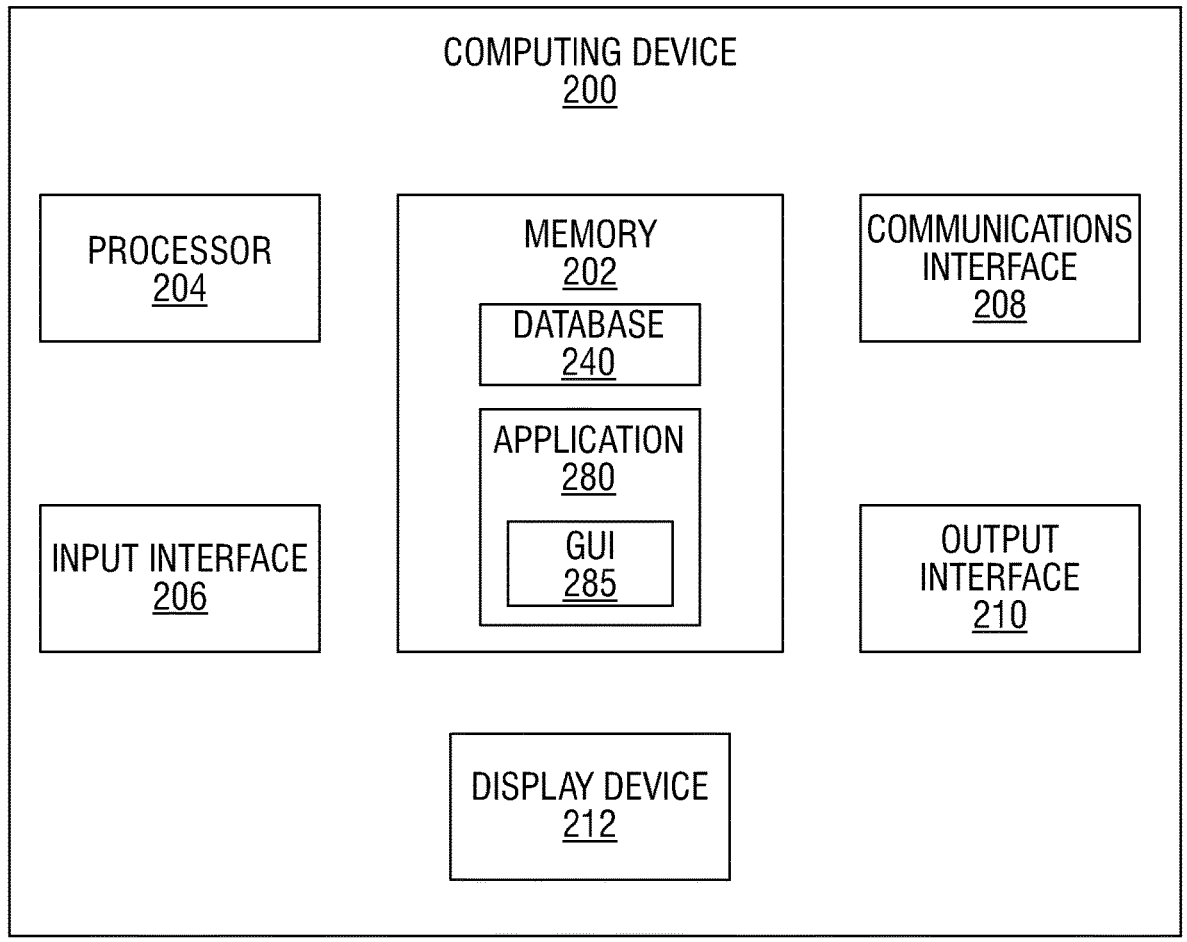
FIG. 2 is a simplified box diagram of an exemplary computing device forming part of the system of FIG. 1.

Turning now to FIG. 2, there is shown a simplified block diagram of the computing device 200. The computing device 200 may include a memory 202, a processor 204, an input interface 206, a communications interface 208, an output interface 210, and a display device 212. The memory 202 may store a database 240 and an application 280. The database may store data regarding the patient, the marker 150, the target tissue 160, the treatment procedure, and/or image data of at least a portion of the patient's body. The application 280 may include instructions for generating a graphical user interface (GUI) 285 which, when executed by the processor 204, cause the display device 212 and/or the display device 250 to display various elements, such as an image guidance view 252 and/or a textual guidance view 254.

The memory 202 may include any non-transitory computer-readable storage media for storing data and/or software that is executable by the processor 204 and which controls the operation of the computing device 200 and/or the structured light scanning device 120. In an embodiment, the memory 202 may include one or more solid-state storage devices such as flash memory chips. Alternatively, or in addition to the one or more solid-state storage devices, the memory 202 may include one or more mass storage devices connected to the processor 204 through a mass storage controller (not shown) and a communications bus (not shown). Although the description of computer-readable media included herein refers to a solid-state storage, it should be appreciated by those skilled in the art that computer-readable storage media may be any available media that is accessible by the processor 204. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the computing device 200.

The input device 206 may be any device by means of which a user of the system 100, such as a clinician, may interact with the computing device 200, such as, for example, a mouse, keyboard, foot pedal, touch screen, and/or voice interface. The communications interface 208 may be configured to connect to a network such as a local area network (LAN) consisting of a wired network and/or a wireless network, a wide area network (WAN), a wireless mobile network, a Bluetooth network, and/or the internet. The output interface 210 may include any connectivity port or bus, such as, for example, parallel ports, serial ports, universal serial busses (USB), or any other similar connectivity port known to those skilled in the art.

Figure 3A:
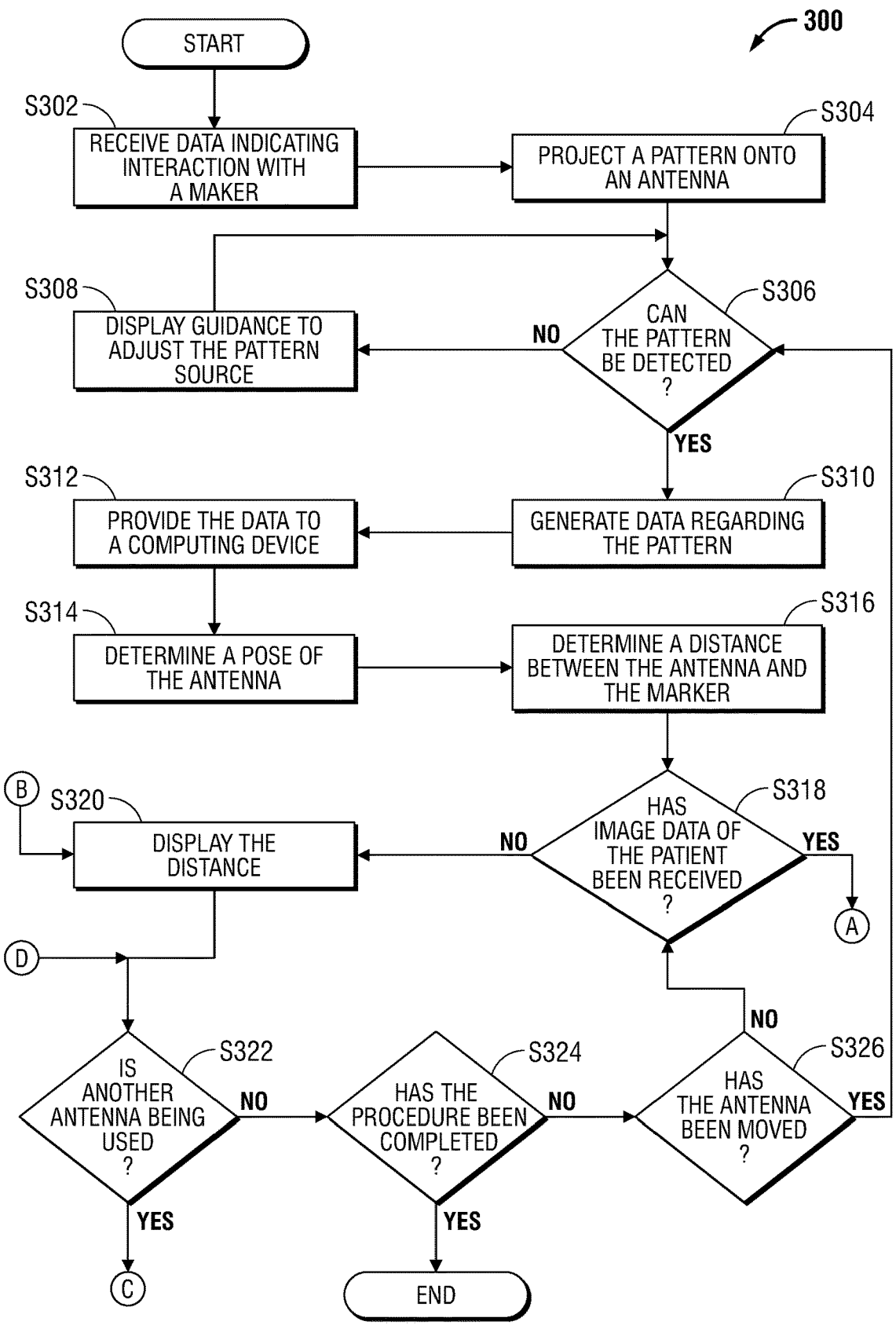
FIGS. 3A and 3B show a flowchart of an exemplary method for locating a target location using structured light scanning, according to an embodiment of the present disclosure.
Figure 3B:
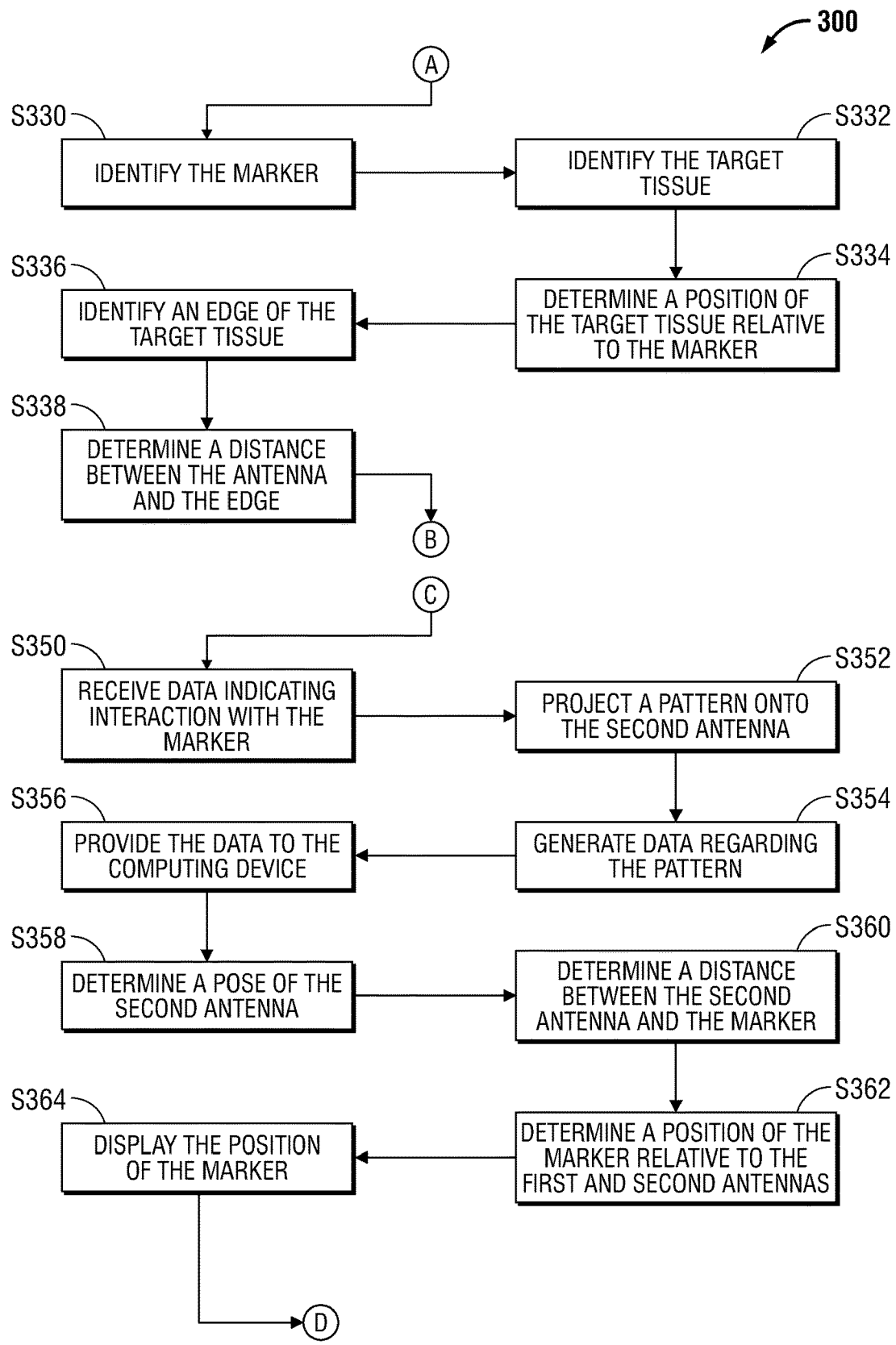

With reference to FIGS. 3A and 3B, there is shown a flowchart of an exemplary method 300 for localizing target tissue, according to an embodiment of the present disclosure. While the various steps of the method 300 are described below in an ordered sequence, those skilled in the art will recognize that some or all of the steps may be performed an a different order or sequence, repeated, and/or omitted without departing from the scope of the present disclosure.

As noted above, one or more markers 150 may be placed inside or proximate to the target tissue 160 prior to the start of the method 300. For example, the marker 150 may be placed using image guidance during a biopsy procedure. Further, image data of at least a portion of the patient's body including the target tissue 160 may be acquired prior to the start of the method 300.

Turning now to FIG. 3A, processing of the method 300 may start at step S302, where the computing device 200 receives data indicating interaction between an antenna 110*a*, 110*b* and the marker 150 at a first location. For example, the computing device 200 may receive data indicating that the antenna 110*a* of the ultrasound probe 130 is interacting with the marker 150. Alternatively, the computing device 200 may receive data indicating that the antenna 110*b* of the surgical tool 140 is interacting with the marker 150. In yet another alternative, in embodiments where the antennas 110*a*, 110*b* are included in a separate device, the computing device 200 may receive data indicating that an antenna 110*a*, 110*b* in such a separate device is interacting with the marker 150. As an exemplary embodiment, the description of steps S304-S320 below will describe an embodiment where the computing device 200 receives data indicating interaction between the antenna 110*a* of the ultrasound probe 130 and the marker 150. For example, the data indicating interaction between the antenna 110*a* of the ultrasound probe 130 at the first location and the marker 150 may indicate a distance between the antenna 110*a* and the marker 150 at the first location, such as based on a signal strength metric. In embodiments where the marker 150 is an RFID device, the marker 150 may provide identification information related to the marker 150 and/or information about the position of the marker 150 relative to the target tissue 160.

Thereafter, or concurrently therewith, at step S304, the structured light pattern source 124 projects the pattern 126 onto the ultrasound probe 130. The computing device 200 may then, at step S306, determine whether the structured light detector 122 is able to detect the pattern 126. If it is determined at step S306 that the structured light detector 122 is not able to detect the pattern 126 ("No" at step S306), processing proceeds to step S308, where the computing device 200 causes the display device 250 to display guidance for adjusting the position and/or orientation of the pattern source relative to the ultrasound probe 130 and/or the surgical tool 140. Thereafter, processing returns to step S306, where it is again determined whether the structured light detector 122 is able to detect the pattern 126.

If it is determined at step S306 that the structured light detector 122 is able to detect the pattern 126 ("Yes" at step S306), processing proceeds to step S310, where the structured light scanning device 120 generates data regarding the pattern 126 detected by the structured light detector 126. In embodiments where the pattern 126 is a set of parallel lines, the data may include data regarding the angular dispersion of the lines and the distance between the lines, as well as distortions to the pattern 126. Those skilled in the art will recognize that there are various other line, cross hatch or point clouds including even progressive single point scanning data points and metrics that are relevant to structured light scanning that may also be included in the data generated by the structured light scanning device 120.

Thereafter, at step S312, the structured light scanning device 120 provides the data to the computing device 200 which, at step S314, determines a pose of the ultrasound probe 130 at the first location relative to the structured light scanning device 120 and/or the structured light detector 122. In some embodiments, the structured light scanning device 120 may include a processor and/or various logic circuits that enable the structured light scanning device 120 determine the pose of the ultrasound probe 130 at the first location relative to the structured light scanning device 120 and/or the structured light detector 122. In such embodiments, the processing of step S314 is performed by the structured light scanning device 120 prior to providing data to the computing device 200, and instead, the structured light scanning device 120 provides the computing device 200 with the determined pose of the ultrasound probe 130 at the first location relative to the structured light scanning device 120 and/or the structured light detector 122.

Thereafter, or concurrently with any of steps S304-S314, at step S316, the computing device 200 determines a distance between the antenna 110*a* (and thus the ultrasound probe 130) at the first location and the marker 150. The determination may be based on the data received at step S302, e.g. a signal and/or a strength of a signal between the antenna 110*a* and the marker 150 at the first location.

Next, at step S318, the computing device 200 determines whether image data of the patient's body has been received. The image data may be live image data, such as image data received from, for example, the ultrasound probe 130. Live image data may also be received from other imaging modalities, such as CBCT, fluoroscopic imaging, and/or any other relevant imaging modality known to those skilled in the art. Alternatively, the image data may be pre-operative image data acquired during a pre-operative scan of one or more portions of the patient's body. If the computing device 200 determines at step S318 that image data of the patient's body has been received ("Yes" at step S318), processing skips ahead to step S330. Alternatively, if computing device 200 determines at step S318 that image data of the patient's body has not been received ("No" at step S318), processing proceeds to step S320.

At step S320, the computing device 200 causes the display device 250 to display the distance between the antenna 110*a* (and thus the ultrasound probe 130) and the marker 150 at the first location determined at step S316. For example, as shown in the textual guidance view 254 displayed on the display device 250 of FIG. 1, the computing device 200 may cause the display device 250 to display the distance determined at step S316 as textual and/or graphical guidance, such as by a distance measure.

Thereafter, at step S322, the computing device 200 determines whether another antenna 110a, 110b is being used during the procedure. For example, if the antenna 110a of the ultrasound probe 130 is used for steps S302-S316, the computing device 200 may determine at step S322 that the antenna 110b of the surgical tool 140 is also being used during the procedure. In some embodiments, step S322 is performed at the start of the procedure, such as for a system diagnostic check, to determine a number of antennas 110a, 110b being used during the procedure. In such embodiments, instead of performing steps S350-S364 after steps S302-S320, steps S350-S364 may be performed concurrent with steps S302-S320. If the computing device 200 determines that another antenna 110a, 110b is being used during the procedure ("Yes" at step S322), processing skips ahead to step S350. Alternatively, if the computing device 200 determines at step S322 that there are no additional antennas being used during the procedure ("No" at step S322), processing proceeds to step S324.

At step S324, the computing device 200 determines whether the surgical procedure has been completed. For example, the computing device 200 may determine, based on input from the clinician provided via the input interface 206 that the surgical procedure has been completed. If the computing device 200 determines at step S324 that the surgical procedure has been completed ("Yes" at step S324), processing of the method 300 ends. Alternatively, if the computing device 200 determines at step S324 that the surgical procedure has not been completed ("No" at step S324), processing proceeds to step S326.

At step S326, the computing device 200 determines whether the antenna 110a, 110b has been moved. For example, the computing device 200 may receive data indicating that the antenna 110a and/or the antenna 110b is interacting with the marker 150, and that the interaction is different from the interaction at step S302. Alternatively or in addition, the computing device 200 may receive data from the structured light scanning device 120 indicating that the structured light detector 122 has detected a change in the pattern 126 projected onto the ultrasound probe 130 and/or the surgical tool 140. If the computing device 200 determines at step S326 that the antenna 110a, 110b has been moved ("Yes" at step S326), processing returns to step S306, where the computing device 200 again determines whether the pattern 126 can be detected. Alternatively, if the computing device 200 determines at step S326 that the antenna 110a, 110b has not been moved, processing returns to step S318, where the computing device 200 again determines whether image data, in this instance new or additional image data, of the patient's body has been received.

Turning now to FIG. 3B, at step S330, the computing device 200 identifies the marker 150 in the image data. For example, if the image data is pre-operative image data, such as image data acquired during a CT scan of a portion of the patient's body, or live image data, such as image data received from the ultrasound sensor 130, the computing device 200, via various image processing techniques known in the art, may analyze the image data to identify the marker 150 in the image data. Additionally or alternatively, the computing device 200 may receive input from the clinician, such as via input interface 206, identifying the marker 150 in the image data.

Thereafter, or concurrently therewith, at step S332, the computing device 200 identifies the target tissue 160 in the image data. For example, the computing device 200, via various image-processing techniques known in the art, may analyze the image data to identify the target tissue 160 in the image data. Additionally or alternatively, the computing device 200 may receive input from the clinician, such as via input interface 206, identifying the target tissue 160 in the image data.

Next, at step S334, the computing device 200 determines a position of the target tissue 160 relative to the marker 150. For example, if the marker 150 is placed proximate the target tissue 160, the computing device 200 may determine a distance and a direction between the marker 150 and the target tissue 160. Alternatively, if the marker 150 is placed in the target tissue 160, the computing device 200 may simply determine that the marker 150 is place in the target tissue 160.

Thereafter, or concurrently with steps S330-S334, at step S336, the computing device 200 identifies an edge of the target tissue 160 in the image data. For example, the computing device 200, via various image-processing techniques known in the art, may analyze the image data to identify one or more edges of the target tissue 160 in the image data. Additionally or alternatively, the computing device 200 may identify an edge of the target tissue 160 based on the position of a marker 150 placed at an edge of the target tissue 160 and/or based on input received from the clinician, such as via input interface 206, identifying the edges of the target tissue 160 in the image data. The input provided by the clinician may be one or more points or trajectories from the surgical tool 140 to the marker 150.

Next, at step S338, the computing device 200 determines a distance between the antenna 110a, 110b (and thus the ultrasound probe 130 and/or the surgical tool 140) and the edges of the target tissue 160 determined at step S336. For example, the computing device 200 may determine the distance between the edges of the target tissue 160 and the antenna 110a, 110b based on the distance between the antenna 110a, 110b and the marker 150 determined at step S316, the position of the target tissue 160 relative to the marker 150 determined at step S334, and/or a distance between the edges of the target tissue 160 and the marker 150. In embodiments where multiple antennas 110a, 110b are being used, the computing device 200 may further determine a direction between the antennas 110a, 110b (and thus the ultrasound probe 130 and the surgical tool 140) and the edges of the target tissue 160. Thereafter, processing returns to step S320, where the computing device 200 causes the display device 250 to display the direction and distance determined at step S338.

At step S350, the computing device 200 receives data indicating interaction between another antenna and the marker 150. For example, the computing device 200 may receive data indicating that the antenna 110b of the surgical tool 140 is interacting with the marker 150 at a second location.

Thereafter, or concurrently therewith, at step S352, the structured light pattern source 124 projects the pattern 126 onto the surgical tool 140. Next, at step S354, the structured light scanning device 120 generates data regarding the pattern 126 detected by the structured light detector 126. Thereafter, at step S356, the structured light scanning device 120 provides the data to the computing device 200 which, at step S358, determines a pose of the surgical tool 140 at the second location relative to the structured light scanning device 120 and/or the structured light detector 122. Similar to step S314, in embodiments where the structured light scanning device 120 includes a processor and/or various logic circuits that enable the structured light scanning device 120 determine the pose of the surgical tool 140 at the second location relative to the structured light scanning device 120 and/or the structured light detector 122, the processing of step S358 is performed by the structured light scanning device 120 prior to providing data to the computing device 200, and instead, the structured light scanning device 120 provides the computing device 200 with the determined pose of the surgical tool 140 at the second location relative to the structured light scanning device 120 and/or the structured light detector 122.

Thereafter, or concurrently with any of steps S352-S358, at step S360, the computing device 200 determines a distance between the antenna 110*b* (and thus the surgical tool 140) at the second location and the marker 150. The determination may be based on a signal and/or a strength of a signal between the antenna 110*b* at the second location and the marker 150.

Next, at step S362, the computing device 200 determines a position of the marker 150 relative to the antenna 110*a* of the ultrasound probe 130 at the first location and the antenna 110*b* of the surgical tool 140 at the second location. For example, the computing device 200 may determine the position of the marker 150 by triangulating the signals received from the interaction between the antennas 110*a*, 110*b*, and the marker 150 and/or based on the distance between the antenna 110*a* at the first location and the marker 150 (determined at step S316) and the distance between the antenna 110*b* at the second location and the marker 150 (determined at step S360). Thereafter, at step S364, the computing device 200 causes the display device 250 to display the position of the marker 150 relative to the antennas 110*a*, 110*b* (and thus the ultrasound probe 130 and the surgical tool 140) as determined at step S362. For example, as shown in the textual guidance view 254 displayed on the display device 250 of FIG. 1, the computing device 200 may cause the display device 250 to display the distance between the antenna 110*b* determined at step S360 as textual and/or graphical guidance, such as by a distance measure, and display an arrow (or other directional indicator) indicating the relative direction of the antenna 110*b* to the target 150. Thereafter, processing returns to step S322, where the computing device 200 again determines if another antenna 110*a*, 110*b* is being used during the procedure.

While the above disclosure describes using multiple antennas 110*a*, 110*b* to determine a distance between the antennas 110*a*, 110*b* and the marker 150 at the first and second locations, it is envisioned that a single antenna 110*a*, 110*b* may be used to determine a distance between the antenna 110*a*, 110*b* and the marker 150 at the first and second locations. For example, after the distance between the antenna 110*a* and the marker 150 at the first location is determined (as described at step S316), it may be determined at step S322 that another antenna 110*b* is not being used, and may further be determined at step S326, based on additional data indicating interaction between the antenna 110*a* and the marker 150, that the antenna 110*a* has been moved to a second location. Thereafter, after processing again proceeds to step S316, a distance between the antenna 110*a* and the marker 150 at the second location may be determined. A position of the marker 150 relative to the antenna 110*a* at the first and second locations may thus be determined using only a single antenna 110*a* to determine a distance between the antenna 110*a* and the marker 150 at the first and second locations. This process may be repeated any number of times for any number of locations to which the antenna 110*a* is moved.

Additional details about the construction, operation, and use of structured light scanning systems are described in commonly-owned U.S. patent application Ser. No. 15/468,981, entitled THORACIC ENDOSCOPE FOR SURFACE SCANNING, filed on Mar. 24, 2017, by Sartor et al., the entire contents of which are incorporated herein by reference. Likewise, additional details about the construction, operation, and use of systems for detecting and interacting with markers placed inside a patient's body are described in commonly-owned U.S. patent application Ser. No. 15/293,939, entitled COMMUNICATING LOCALIZATION MARKERS, filed on Oct. 14, 2016, by William Dickhans, the entire contents of which are incorporated herein by reference.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

What is claimed is:

1. A surgical system, comprising:
   a computing device including a processor and a memory storing instructions which, when executed by the processor, cause the computing device to:
   receive first data from an antenna indicating that the antenna is interacting with a marker at a first location;
   determine a distance between the antenna and the marker at the first location;
   detect a first pattern projected onto the antenna;
   determine, based on the detected first pattern, a pose of the antenna at a first location;
   receive second data from the antenna indicating that the antenna is interacting with the marker at a second location;
   determine a distance between the antenna and the marker at the second location;
   detect a second pattern projected onto the antenna;
   determine, based on the detected second pattern, a pose of the antenna at the second location; and
   determine, based on the determined distance between the antenna and the marker at the first location and the second location, and the determined pose of the antenna at the first location and the second location, a position of the marker relative to the antenna.

2. The system according to claim 1, wherein the instructions, when executed by the processor, further cause the computing device to display the determined position of the marker relative to the antenna.

3. The system according to claim 1, wherein the instructions, when executed by the processor, further cause the computing device to:
   receive image data of at least a portion of a patient's body;
   identify the marker in the image data;
   identify a target tissue in the image data;
   determine a position of the target tissue relative to the marker;
   determine a distance between the antenna and the target tissue; and
   display the determined distance between the antenna and the target tissue.

4. The system according to claim 3, wherein the distance between the antenna and the target tissue is determined based on the determined position of the target tissue relative to the marker.

5. The system according to claim 1, wherein the instructions, when executed by the processor, further cause the computing device to:

receive image data of at least a portion of a patient's body;
identify the marker in the image data;
identify an edge of a target tissue in the image data;
determine a position of the edge of the target tissue relative to the marker;
determine a distance between the antenna and the edge of the target tissue; and
display the determined distance between the antenna and the edge of the target tissue.

6. The system according to claim 5, wherein the distance between the antenna and the edge of the target tissue is determined based on the determined position of the edge of the target tissue relative to the marker.

7. The system according to claim 3, further comprising:
an ultrasound device,
wherein the antenna is included in the ultrasound device, and
wherein the image data is received from the ultrasound device.

8. The system according to claim 1, wherein the antenna is a high-gain directional antenna.

9. The system according to claim 1, wherein the antenna is included in a surgical tool or an ultrasound device.

10. The system according to claim 1, wherein the marker is a radio frequency identification (RFID) device.

11. The system according to claim 1, wherein the instructions, when executed by the processor, further cause the computing device to determine a position and an orientation of the antenna relative to a structured light detector by determining a distortion of at least a portion of the pattern projected onto the antenna.

12. The system according to claim 1, wherein the first data includes a signal strength metric and the distance between the antenna and the marker at the first location is determined based on the signal strength metric.

13. The system according to claim 1, wherein the instructions, when executed by the processor, further cause the computing device to determine an orientation of the marker relative to the antenna based on the first data or the second data.

14. The system according to claim 1, further comprising:
a structured light pattern source configured to project the first pattern and the second pattern; and
a structured light detector configured to detect the projection of the first pattern and the second pattern.

15. The system according to claim 14, wherein the structured light detector includes at least one of an infrared imaging device, a laser, or an LED laser emitting a collimated beam.

16. A system, comprising:
an antenna configured to interact with a marker placed proximate target tissue inside a patient's body; and
a computing device including a processor and a memory storing instructions which, when executed by the processor, cause the computing device to:
receive first data from the antenna indicating that the antenna is interacting with the marker at a first location;
detect a first pattern projected onto the antenna;
determine, based on the detected first pattern, a pose of the antenna at a first location;
receive second data from the antenna indicating that the antenna is interacting with the marker at a second location;
detect a second pattern projected onto the antenna;
determine, based on the detected second pattern, a pose of the antenna at the second location; and
determine, based on the determined pose of the antenna at the first location and the second location, a position of the marker relative to the antenna.

17. The system according to claim 16, wherein the instructions, when executed by the processor, further cause the computing device to display the determined position of the marker relative to the antenna.

18. The system according to claim 16, wherein the instructions, when executed by the processor, further cause the computing device to:
receive image data of at least a portion of the patient's body;
identify the marker in the image data;
identify the target tissue in the image data;
determine a position of the target tissue relative to the marker;
determine a distance between the antenna and the target tissue; and
display the determined distance between the antenna and the target tissue.

19. The system according to claim 18, wherein the distance between the antenna and the target tissue is determined based on the determined position of the target tissue relative to the marker.

20. A surgical system, comprising:
a computing device including a processor and a memory storing instructions which, when executed by the processor, cause the computing device to:
receive first data from an antenna indicating that the antenna is interacting with the marker at a first location;
detect a first pattern projected onto the antenna;
determine, based on the detected first pattern, a pose of the antenna at a first location;
receive second data from the antenna indicating that the antenna is interacting with the marker at a second location;
detect a second pattern projected onto the antenna;
determine, based on the detected second pattern, a pose of the antenna at the second location;
determine, based on the determined pose of the antenna at the first location and the second location, a position of the marker relative to the antenna; and
display the determined position of the marker relative to the antenna.

* * * * *